United States Patent
Chassagnon et al.

(10) Patent No.: US 11,017,528 B2
(45) Date of Patent: May 25, 2021

(54) METHOD AND DEVICE FOR PROCESSING AT LEAST ONE IMAGE OF A GIVEN PART OF AT LEAST ONE LUNG OF A PATIENT

(71) Applicants: Universite Paris Descartes, Paris (FR); Intrasense, Montpellier (FR); Assistance Publique-Hopitaux de Paris, Paris (FR)

(72) Inventors: Guillaume Chassagnon, Paris (FR); Marie-Pierre Revel, Paris (FR); Stéphane Chemouny, Montpellier (FR); Amandine René, Castries (FR)

(73) Assignees: Universite Paris Descartes; Intrasense; Assistance Publique-Hopitaux de Paris

( * ) Notice: Subject to any disclaimer, the term of this patent is extended or adjusted under 35 U.S.C. 154(b) by 75 days.

(21) Appl. No.: 16/339,615

(22) PCT Filed: Oct. 4, 2017

(86) PCT No.: PCT/EP2017/075246
§ 371 (c)(1),
(2) Date: Apr. 4, 2019

(87) PCT Pub. No.: WO2018/065482
PCT Pub. Date: Apr. 12, 2018

(65) Prior Publication Data
US 2020/0051240 A1 Feb. 13, 2020

(30) Foreign Application Priority Data
Oct. 4, 2016 (FR) ...................................... 1659565

(51) Int. Cl.
*G06T 7/00* (2017.01)
*G06T 7/162* (2017.01)
(Continued)

(52) U.S. Cl.
CPC ............ *G06T 7/0012* (2013.01); *A61B 6/032* (2013.01); *A61B 6/541* (2013.01); *G06T 7/11* (2017.01);
(Continued)

(58) Field of Classification Search
None
See application file for complete search history.

(56) References Cited

U.S. PATENT DOCUMENTS

| 2013/0004044 A1* | 1/2013 | Ross ....................... G06T 7/136 |
| | | 382/131 |
| 2016/0203263 A1* | 7/2016 | Maier ................... G06F 19/321 |
| | | 705/2 |

OTHER PUBLICATIONS

DeBoer et al ("Automated CT Scan Scores of Bronchiectasis and Air Trapping in Cystic Fibrosis", Chest, pp. 593-603, XP055385812, Published Mar. 3, 2014) (Year: 2014).*
(Continued)

*Primary Examiner* — Leon Viet Q Nguyen
(74) *Attorney, Agent, or Firm* — Lerner, David, Littenberg, Krumholz & Mentlik, LLP (57) ABSTRACT

A method for automatically processing at least one image slice of a given part of at least one lung of a patient suffering from a pathology that causes a bronchial infection by diffuse dilatation of the bronchial tubes of the lungs. The method includes segmenting the at least one image slice of the given part of the lung, in order to produce a histogram characterizing the pulmonary density of the given part of the lunch, by means of the voxels of the at least one image slice, each voxel associated with a given pulmonary density; calculating a threshold, from the histogram, corresponding to a threshold pulmonary density, based on at least one characteristic of the histogram, a first characteristic being the mode of the histogram; determining from the at least one image slice of the given part of the lung, a pulmonary volume having a pulmonary density higher or lower than the calculated threshold, corresponding to the sum of the voxels
(Continued)

having a pulmonary density higher or lower than the calculated threshold; and calculating an automatic score on the basis of the determined pulmonary volume.

11 Claims, 5 Drawing Sheets

(51) Int. Cl.
    *G06T 7/62*     (2017.01)
    *G06T 7/11*     (2017.01)
    *A61B 6/03*     (2006.01)
    *A61B 6/00*     (2006.01)

(52) U.S. Cl.
    CPC ............... *G06T 7/162* (2017.01); *G06T 7/62* (2017.01); *G06T 2207/10081* (2013.01); *G06T 2207/20072* (2013.01); *G06T 2207/30061* (2013.01)

(56) References Cited

OTHER PUBLICATIONS

Deboer et al: "Automated CT Scan Scores of Bronchiectasis and Air Trapping in Cystic Fibrosis" Chest, Mar. 1, 2014 (Mar. 1, 2014), pp. 593-603, XP055385812, Retrieved from the Internet: URL:https://www.ncbi.nlm.nih.gov/pmc/articles/PMC3941250/pdf /ches_145_3_ 593.pdf.
International Search Report corresponding to PCT/EP2017/075246 dated Nov. 24, 2017, 4 pages.
Zavaletta et al: " High Resolution Multidetector CT-Aided Tissue Analysis and Quantification of Lung Fibrosis", Academic Radiology, Elsevier, Amsterdam, NL, vol. 14, No. 7, Jul. 13, 2007 (Jun. 13, 2007), pp. 772-787, XP022115204, ISSN: 1076-6332.

\* cited by examiner

METHOD AND DEVICE FOR PROCESSING AT LEAST ONE IMAGE OF A GIVEN PART OF AT LEAST ONE LUNG OF A PATIENT

CROSS-REFERENCE TO RELATED APPLICATIONS

The present application is a national phase entry under 35 U.S.C. § 371 of International Application No. PCT/EP2017/075246, filed Oct. 4, 2017, which claims priority from French Patent Application No. 1659565, filed Oct. 4, 2016, all of which are incorporated herein by reference.

FIELD OF THE INVENTION

The present invention concerns a method and a device for processing at least one image of a given part of at least one lung.

The method according to the invention is used to monitor pathologies that induce diffuse bronchiectasis.

STATE OF THE ART

Cystic fibrosis, with an incidence of 1/4500, is the most common serious inherited genetic disease in the Caucasian population. The life expectancy of patients has increased significantly since its description in 1938, now reaching just over 40 years of age and, today, the population of adults with cystic fibrosis is higher than that of children. Respiratory damage remains the most important cause of death. While the lungs of affected individuals are more or less undamaged at birth, the increased viscosity of bronchial secretions leads to their accumulation in the airways and the formation of mucous plugs, or mucoid impactions. Infections, and in particular chronic *Pseudomonas aeruginosa* infection, promoted by defective mucociliary clearance, maintain and aggravate mucoid impactions and bronchial inflammation. Chronic bronchial infection and inflammation gradually lead to the development of bronchial dilatation (bronchiectasis) and terminal respiratory failure. The main objective of patient respiratory management is to control chronic lung infection by administering antibiotics and draining lung secretions. The most recent treatments developed aim to act upstream to correct the viscosity of secretions, and no longer only to act on the consequences.

To evaluate cystic fibrosis-related lung injury, several visual scores have been proposed, including the Brody II score, described in the document "High-resolution computed tomography in young patients with cystic fibrosis: distribution of abnormalities and correlation with pulmonary function tests", by Brody, Klein, Molina et al.

However, the method described in that document has some disadvantages:
- It is time-consuming to implement (about 20 minutes) and is therefore not compatible with use outside research protocols.
- It requires training in a reference center and then repeated practice to be implemented reproducibly, so few experts capable of using it are available in the field.

In addition, the document "Automatic CT scan scores of bronchiectasis and air trapping in cystic fibrosis" proposed a standard method for processing an image of a lung in which a histogram of the image is created, and in which a peak of this histogram is used to calculate a score to diagnose whether the patient whose lung is shown in the image has cystic fibrosis.

DISCLOSURE OF THE INVENTION

One purpose of the invention is to overcome at least one of the above disadvantages.

Therefore, the invention relates to a method for automatically processing at least one image slice of a given part of at least one lung of a patient with a pathology that induces bronchial damage by diffuse dilatation of the bronchi of the lungs, the method comprising steps of:
- acquisition of at least one image slice by CT scan,
- segmentation of the image slice(s) of the given part of the lung, in order to produce a histogram characterizing the lung density of the given part of the lung, using the voxels of the image slice(s), each voxel being associated with a given lung density,
- calculation, from the histogram, of a threshold corresponding to a threshold lung density, based on one or more characteristics of the histogram, a first characteristic being the mode of the histogram, the mode corresponding to the lung density most represented in the histogram of the image(s) of the given part of the lung, and a second characteristic being a standard deviation of the density values of the histogram,
- determination, from the image slice(s) of the given part of the lung, of a lung volume having a lung density above or below the calculated threshold, corresponding to the sum of the voxels having a lung density above or below the calculated threshold,
- calculation, from the determined lung volume, of an automatic score to monitor changes in the patient's bronchial involvement.

The proposed method has many advantages:
- It can be implemented automatically, without requiring an expert;
- It can be executed quickly;
- It is perfectly reproducible (the automatic score obtained requires no manual correction).

Furthermore, making the threshold dependent not only on the mode of the histogram but also on the standard deviation of the histogram data allows for variations in the "spread" of the histogram, these variations being related to the degree of inspiration). This increases the correlation between the automatic score obtained on the basis of this threshold and the FEV1 of the patient concerned, and consequently the reliability of the automatic score.

DESCRIPTION OF THE FIGURES

Other features, purposes and advantages of the invention will emerge from the following description, which is purely illustrative and non-limiting, and which must be read in conjunction with the annexed drawings on which.

On all figures, similar elements have the same reference signs.

DETAILED DESCRIPTION OF THE INVENTION

Image Acquisition and Processing System

Figure 1:
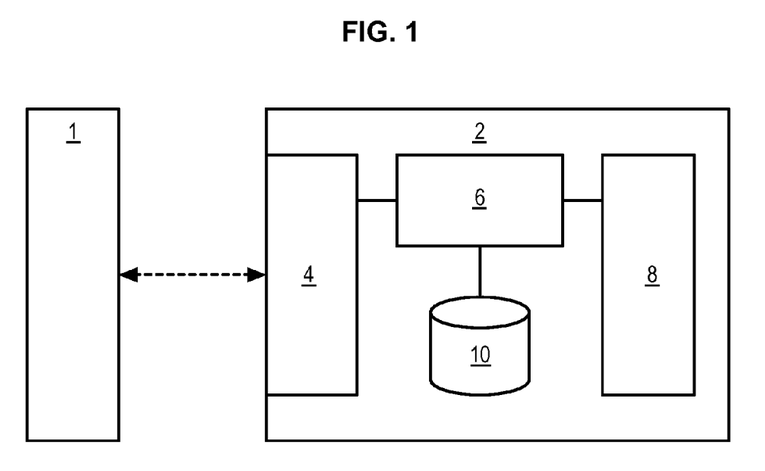
FIG. 1 schematically represents an image acquisition and processing system according to one embodiment of the invention.

Referring to FIG. 1, a system comprises a lung image acquisition device 1, and an image processing device 2.

The image acquisition device 1 is known from the state of the art; this device 1 is for example an X-ray scanner or a magnetic resonance imaging (MRI) device.

The image processing device 2 is configured to process images acquired by the device 1.

The image processing device 2 comprises a communication interface 4 with the acquisition device 1, a segmentation module 6, a processor 8, and a memory 10.

The communication interface 4 is suitable for receiving images acquired by the acquisition device 1. This communication interface 4 is for example wired or wireless (Wi-Fi, etc.). In a particular variant embodiment, the devices 1 and 2 form two internal components of a single device.

The segmentation module 6 is configured to analyze the content of images provided by the acquisition device 1 and to extract certain information therefrom.

For example, the segmentation module 6 is configured to run the Myrian® computer program or the Syngo.via® program, which are known from the state of the art. Other alternative segmentation programs known from the state of the art can be used by the segmentation module 6.

The processor 8 is configured to perform calculations based on this information.

The memory 10 is suitable for storing images or calculation data produced by the segmentation module 6 and/or the processor 8.

Image Acquisition and Processing Method

Figure 2:
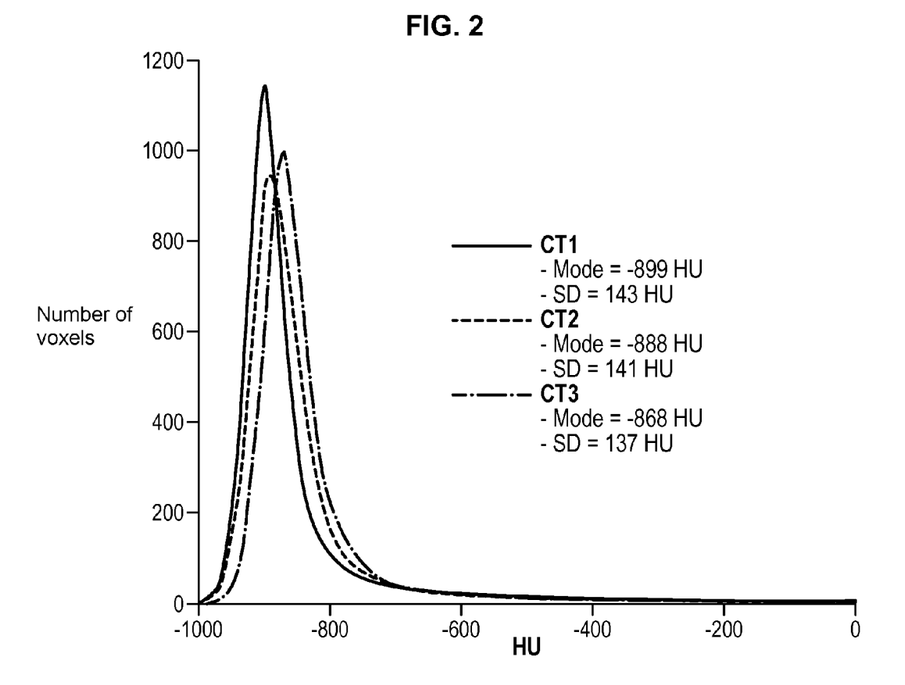
FIG. 2 shows three lung density histograms for a patient with the number of voxels on the y-axis.
Figure 3:
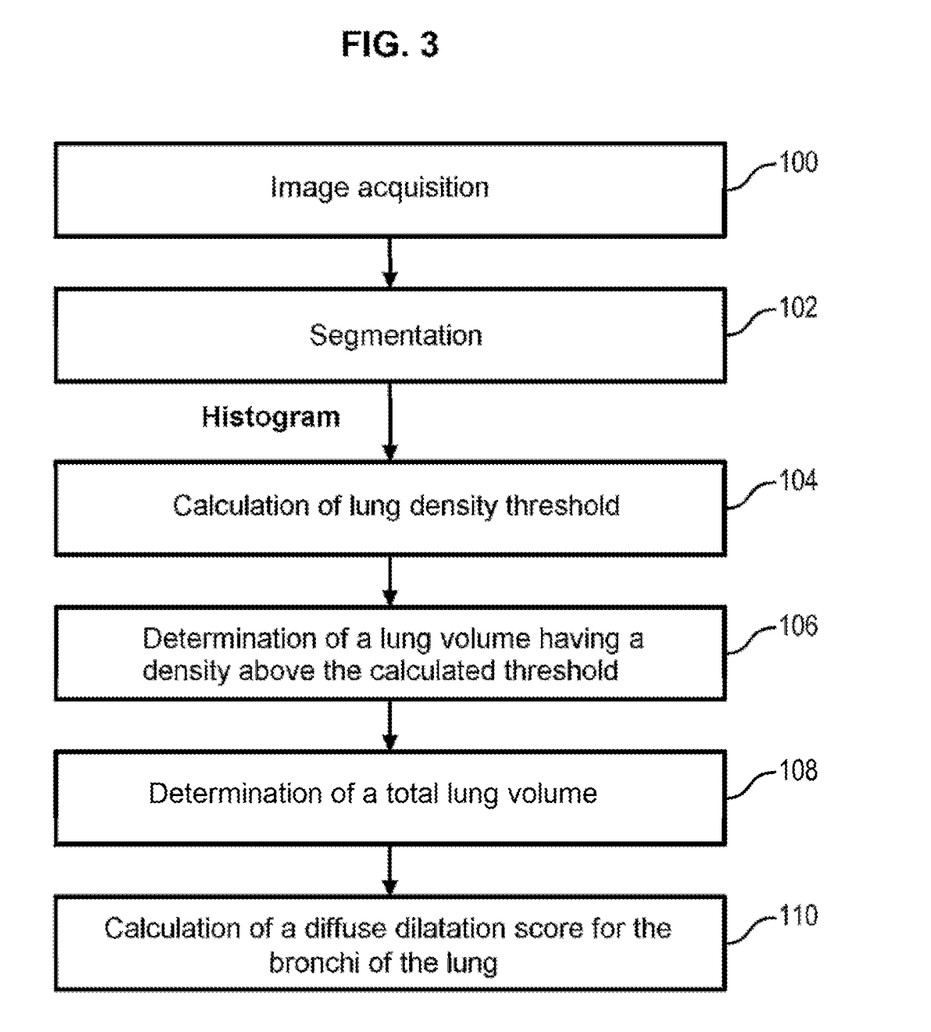
FIG. 3 is a flowchart of steps of an automatic image processing method according to one embodiment of the invention.

Referring to FIG. 2, an automatic image acquisition and processing method consists of the following steps.

The device 1 acquires at least one image of at least a given part of at least one lung of a patient.

Preferably, the one or more images were acquired when the patient inspires. It will be seen below that this increases the reliability of the method's output data.

The images are slices of a certain thickness; the images differ according to the slice thicknesses considered for the images.

The images show both lungs together or show one or more lobes of the lungs.

The following example considers the example of the acquisition of a plurality of 2D images showing different slices of the same lung.

The images are CT images. Alternatively, an MRI could be used for the invention.

Each received image is typically grayscale.

In each image of the plurality of images, a near-black pixel or voxel is representative of a portion of the lung represented on this image that is not very dense. Conversely, a near-white pixel or voxel is representative of a portion of the lung represented on this image that is very dense.

The plurality of 2D images forms a three-dimensional image comprising a plurality of voxels, each voxel referring to an elementary volume of the lung represented by the images. Thus, similarly, each voxel of the plurality of images has a gray level; a near-black voxel is representative of an elementary volume of the lung that is not very dense, and, conversely, a near-white voxel is representative of an elementary volume of the lung that is very dense.

The plurality is transmitted to the segmentation module 6 via the communication interface 4.

The segmentation module 6 segments the plurality of images it receives, so as to produce, on the basis of these images, a histogram characterizing lung density from the plurality of images.

The histogram is a curve with a lung density, expressed in Hounsfield units (HU), on the x-axis and a number of voxels on the y-axis. In other words, the histogram indirectly enumerates, for each gray level represented in the image, the number of voxels of the plurality of images having that gray level.

The histogram usually has a general Gaussian shape.

Three examples of histograms characterizing lung density are shown in FIG. 2, corresponding to three pluralities of images acquired in a patient without lung disease who had 3 scans at 1-year intervals (CT1, CT2 and CT3). The modes associated with these three histograms are −899 HU, −888 HU and −868 HU, respectively.

The mode, or dominant value, of the histogram is the lung density of the histogram associated with the greatest number of voxels in this histogram. This mode is therefore indicative of the gray level that occurs most frequently in the plurality of images.

The mode is determined by the segmentation module 6 or by the processor 8.

The segmentation module 6 or the processor 8 also determines the standard deviation of the density values of the histogram.

The processor calculates a lung density threshold based on one or more characteristics of the histogram.

A first characteristic used by the method is the mode of the histogram. The lung density threshold may also depend on the standard deviation of the density values of the histogram, which is a second characteristic used by the method.

For example, the threshold is calculated by the processor 8 as follows:

$$\text{threshold} = \text{mode} + N \cdot (\text{standard deviation})$$

where N is a predetermined value.

The threshold is thus used to separate the voxels of the histogram into 2 groups.

Preferably, N is comprised in an interval ranging from 0 to 4 and the threshold is a high threshold. Very preferentially, N is comprised in an interval ranging from 1 to 3.

When N is strictly positive, the threshold is therefore a density value that is shifted to the right on the histogram; when N is strictly negative, the threshold is therefore a density value that is shifted to the left on the histogram and the threshold is a low threshold. In both cases, this threshold is thus associated with a number of voxels lower than the maximum of the histogram.

Advantageously, N is positive and the density of the lung volume is above this threshold. Indeed, the developed method is based on the study of lung density distributions and is particularly suitable for quantifying the proportion of lungs with too high a density. This proportion of over-dense lung, which is a reflection of the proportion of diseased lung, is obtained by using an individualized threshold calculated on the properties of the histogram of each examination. This individualized threshold responds to the main problem encountered in CT quantification, which is the variability of the distribution of lung densities as a function of the degree of inspiration, making the use of non-individualized thresholds inefficient.

The processor then calculates a ratio between the lung volume with a defined lung density in relation to the calculated threshold and a total lung volume shown in the image.

Total lung volume is estimated by the segmentation module, for example, or predetermined by other means known from the state of the art.

The processor also determines, from the images of the lung, a lung volume with a lung density above or below the calculated threshold.

To that end, the processor can count the total number of voxels in the part of the histogram to the right of the calculated threshold and multiply this number by the elementary volume of a voxel.

The processor also determines a total lung volume shown by the plurality of images.

To that end, the processor can count the total number of voxels counted in the histogram and multiply this number by the elementary volume of a voxel.

The processor then calculates a bronchial dilatation score from the total volume and the lung volume with a lung density above or below the calculated threshold.

The calculated score is stored in the memory 10.

In a first particularly simple embodiment of implementation, the score is calculated as follows:

$$score = \frac{\text{lung volume with a lung density above or below the calculated threshold}}{\text{total lung volume of the lung shown by the set of analyzed images}}$$

Advantageously, the score is calculated as follows:

$$score = \frac{\text{lung volume with a lung density above or below the calculated threshold}}{\text{total lung volume of the lung shown by the set of analyzed images}}$$

In this case, the greater the state of disease, and thus density, of the lung, the higher the score.

Validation of the Results Obtained by the Image Processing Method

To test the validity of the automatic score obtained by implementing the above method, the following protocol was implemented.

Two independent patient cohorts were examined: a development cohort and a second cohort.

The development cohort is a multicenter cohort of longitudinally followed patients (at least 2 examinations available per patient, 40 scans analyzed in total) with scans performed before and after treatment with a drug (ivacaftor) effective for the treatment of those patients with a particular mutation: the G551D mutation of the CFTR gene involved in cystic fibrosis. The objective was to verify that the clinical and functional improvement under treatment was also observed with the dilatation score obtained by the image processing method described above.

The second cohort is an independent single-center cohort corresponding to a set of patients assessed at Cochin Hospital in Paris in 2013, as part of their follow-up every 2 years (53 patients).

For each patient in these two cohorts, a respiratory functional assessment with forced expiratory volume in 1 second (FEV1) study was performed on the same day as the scan. FEV1 is a reference standard, recommended by both the Food and Drug Administration and the European Medicines Agency, for estimating the severity of cystic fibrosis in clinical research protocols.

The correlation between lung density score and FEV1 was measured by calculating the Spearman correlation coefficient (noted rho) using well-known methods.

TABLE 1

Correlation between scores and FEV1

| # | Score | | Rho | p-value |
|---|---|---|---|---|
| | Threshold | | | |
| 1 | (−) 300 HU | 3.17% (±1.10) | −0.53 | <.001 |
| 2 | (−) 400 HU | 4.10% (±1.42) | −0.55 | <.001 |
| 3 | (−) 500 HU | 5.39% (±1.85) | −0.56 | <.001 |
| 4 | MLD + 2.5 SD | 4.02% (±0.55) | −0.61 | <.001 |
| 5 | MLD + 2 SD | 5.10% (±0.80) | −0.64 | <.001 |
| 6 | MLD + 1.5 SD | 6.57% (±1.08) | −0.65 | <.001 |
| 7 | Mode + 3 SD | 4.09% (±0.65) | −0.67 | <.001 |
| 8 | Mode + 2 SD | 6.58% (±1.35) | −0.67 | <.001 |
| 9 | Mode + 1.5 SD | 8.90% (±1.96) | −0.65 | <.001 |
| 10 | Mode + 1 SD | 13.43% (±3.49) | −0.70 | <.001 |
| | Visual method | | | |
| 11 | Brody-II score | 30.65 (±13.76) | −0.76 | <.001 |

Table 1 above lists, for several types of calculated thresholds, the associated bronchial dilatation score obtained (value in % plus or minus standard deviation (SD)), and the value of the rho correlation coefficients with FEV1:
  of the thresholds of predetermined values (columns 1 to 3),
  of the thresholds depending on the mean lung density (MLD) (lines 4 to 6) and the standard deviation of the histogram data,
  of the thresholds, according to other embodiments of the invention, depending both on the mode of the histogram and also on the standard deviation of the histogram data (lines 7 to 10).

Table 1 also lists the correlation coefficient between the Brody-II score and FEV1 (line 11).

Table 1 illustrates that the automatic scores calculated in accordance with the invention (line 10) are more strongly correlated with FEV1 than the bronchial dilatation scores calculated on the basis of fixed thresholds or those depending on mean lung density (MDL).

One reason for this is that the lung density distribution not only varies from one patient to another, but also varies over time within the same patient. This distribution is influenced by disease-related changes (e.g. bronchial thickening increases lung density), but also by technical parameters (parameters used during image acquisition) and by physiological parameters such as the degree of inspiration of the lungs. Indeed, tests carried out in patients without lung disease show that their lung density histogram varies over time (as shown in the three histograms presented in FIG. 2) due to variations in technical and physiological parameters.

Making the threshold depend on parameters specific to the person being examined, namely the mode and advantageously the standard deviation of the histogram, thus allows for interpatient variation (variation related to the degree of inspiration of the patients) and variations in technical parameters. Thus, the automatic score obtained on the basis of such an adaptive threshold remains correlated with FEV1 over time, even if the patient inspires differently or if the above-mentioned technical parameters change.

In addition, making the threshold dependent not only on the mode of the histogram but also on the standard deviation of the histogram data allows for variations in the "spread" of the histogram, these variations being related to the degree of inspiration). This further increases the correlation between the automatic score obtained on the basis of this threshold and FEV1. In Table 1, the embodiment wherein N=3 provides the best correlation results with FEV1.

Moreover, Table 1 illustrates that the value of the correlation coefficients between the different bronchial dilatation scores according to the embodiments of the invention (line 10) and FEV1 are close to the correlation values between the Brody II score and FEV1 (line 11), and this independently of the segmentation program used. In other words, the automatic score obtained by implementing the image processing method described above is of equivalent relevance to that of the Brody-II score, but much easier to obtain than the latter.

Table 2 below examines not the correlation of instant scores with FEV1, as in Table 1, but the correlation of the variation of these same scores (Δscore) over a follow-up period of 19 months on average, with the variation of FEV1 over the same period.

TABLE 2

Correlation between score variations and FEV1 variations

| # | | Δ Score | Rho | p-value |
|---|---|---|---|---|
| | Threshold | | | |
| 1 | (−) 300 HU | −0.24 (±1.03) | −0.44 | 0.030 |
| 2 | (−) 400 HU | −0.38 (±1.23) | −0.55 | 0.004 |
| 3 | (−) 500 HU | −0.46 (±1.48) | −0.53 | 0.006 |
| 4 | MLD + 2.5 SD | −0.15 (±0.44) | −0.55 | 0.005 |
| 5 | MLD + 2 SD | −0.23 (±0.58) | −0.51 | 0.008 |
| 6 | MLD + 1.5 SD | −0.33 (±0.73) | −0.52 | 0.007 |
| 7 | Mode + 3 SD | −0.18 (±0.50) | −0.61 | 0.001 |
| 8 | Mode + 2 SD | −0.31 (±0.83) | −0.58 | 0.002 |
| 9 | Mode + 1.5 SD | −0.36 (±0.99) | −0.47 | 0.017 |
| 10 | Mode + 1 SD | −0.27 (±1.31) | −0.31 | 0.129 |
| | Visual method | | | |
| 11 | Δ Brody-II score | −2.85 (±5.55) | −0.52 | 0.008 |

The data in Table 2 are consistent with those in Table 1: the variation in the automatic score according to one or the other of the different embodiments of the invention is strongly correlated with the variation in FEV1.

Figure 4:
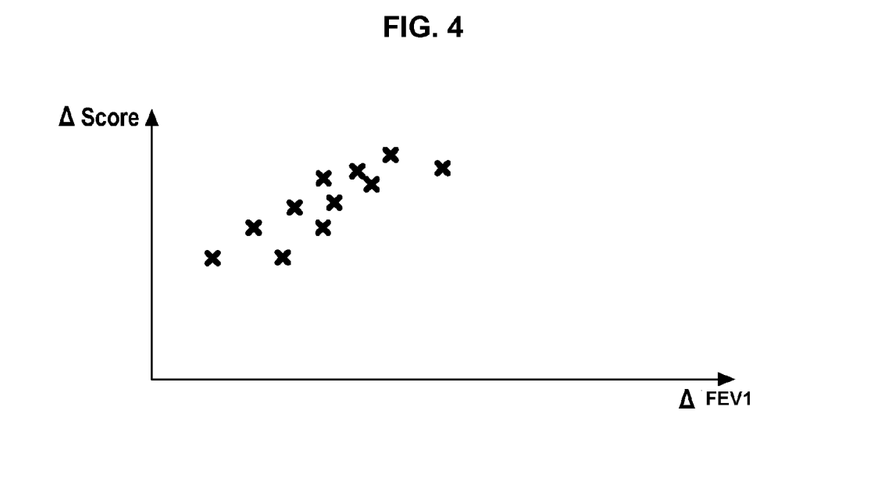
FIG. 4 is a correlation plot between changes in an automatic score to qualify bronchial involvement, obtained by an automatic image processing method according to one embodiment of the invention, and changes in the corresponding forced expiratory volume in 1 second (FEV1).

FIG. 4, by way of example, illustrates a plot showing the correlation between changes in an automatic score obtained by the image processing method according to one embodiment of the invention and changes in FEV1.

Figure 5:
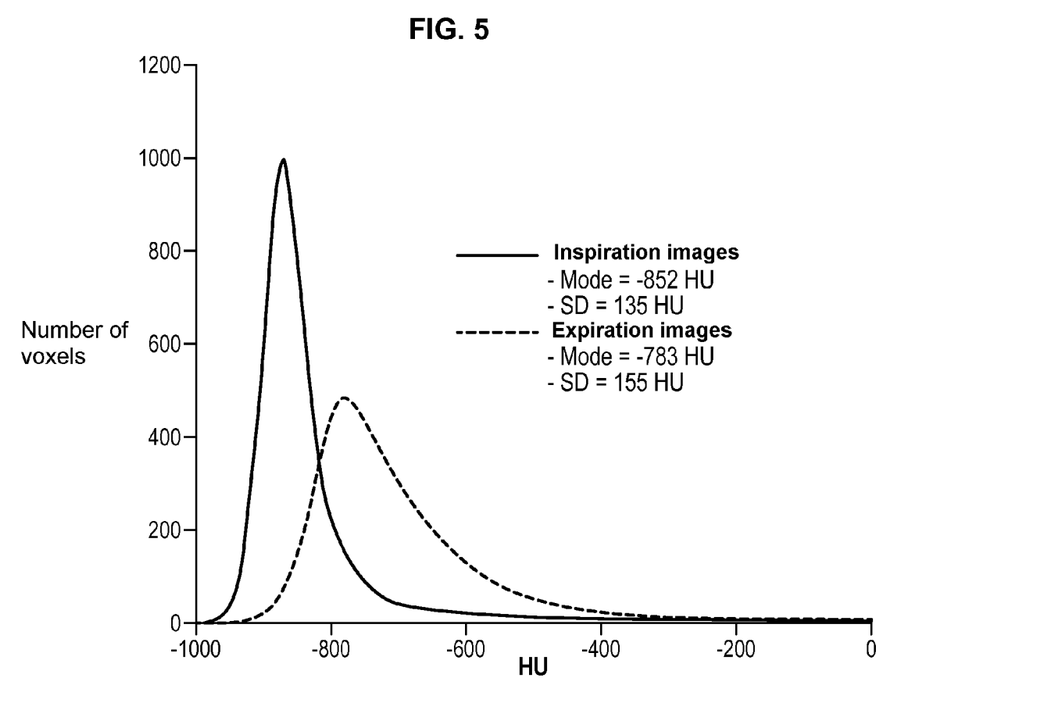
FIG. 5 shows two lung density histograms for a patient.
Figure 6:
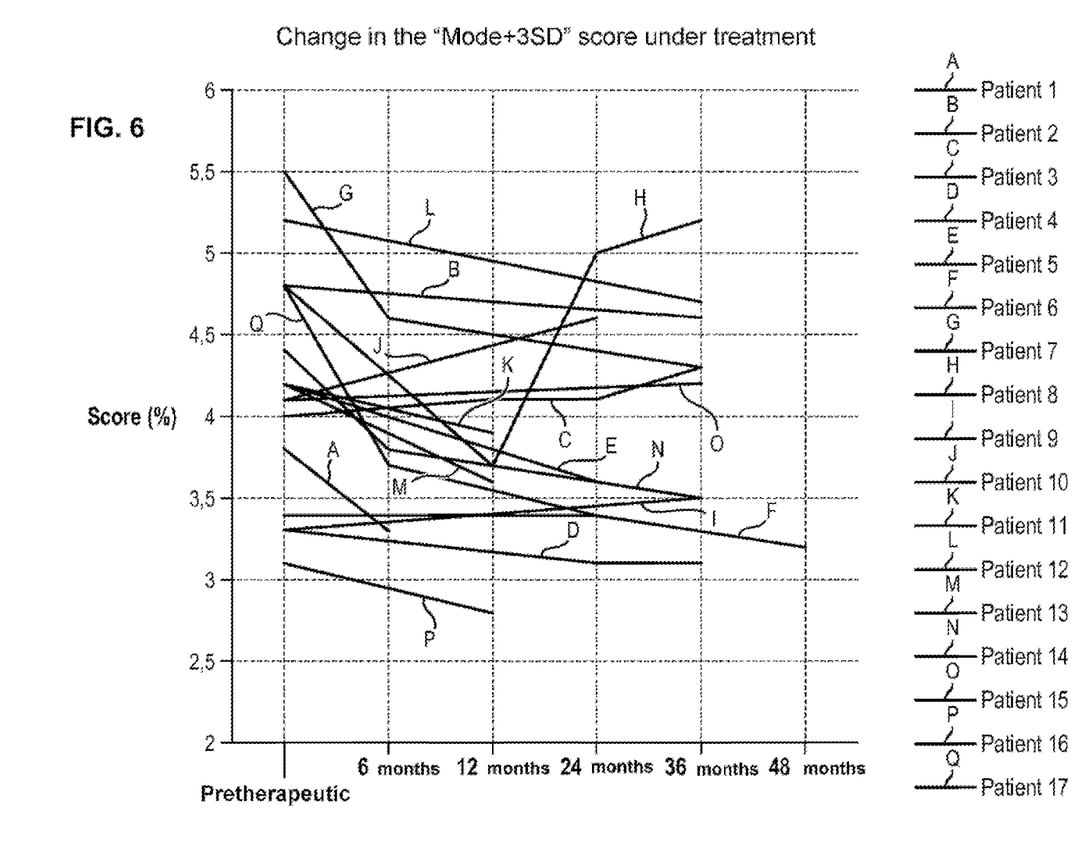
FIG. 6 is a graph of changes over time in the value of dilatation scores calculated for different patients using a processing method according to a first embodiment of the invention.
Figure 7:
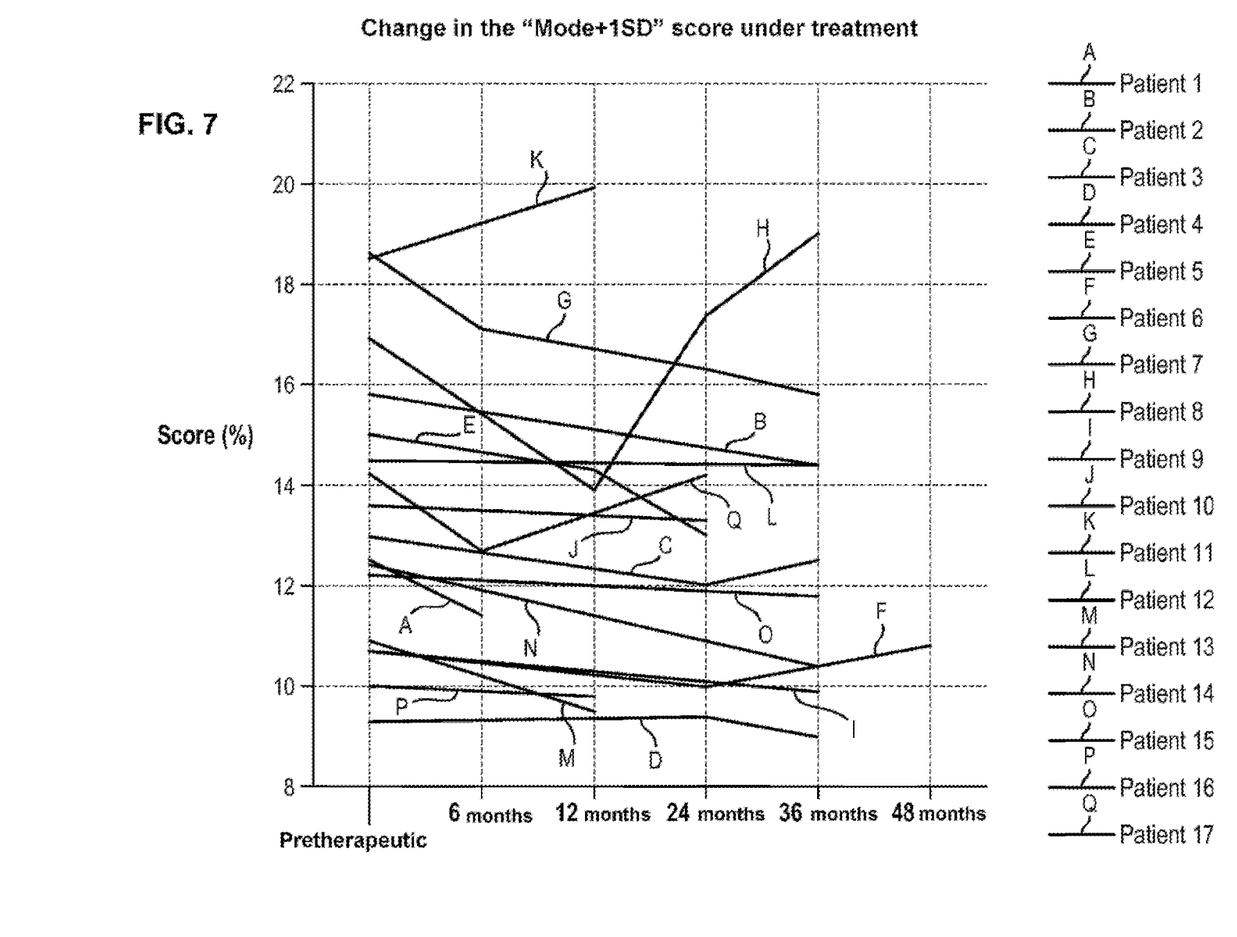
FIG. 7 is a graph of changes over time in the value of dilatation scores calculated for different patients using a processing method according to a second embodiment of the invention.

In addition, FIG. 5 shows two histograms for the same patient, but produced by the segmentation module 6 from images acquired while the patient is inspiring and while the patient is expiring, respectively. It can be seen that these two histograms are different. In particular, the histogram obtained from the inspiration images has a smaller standard deviation than the histogram obtained from the expiration images.

As mentioned above, images are preferably acquired while the patient inspires. This improves the correlation between the automatic score obtained and FEV1.

Other Embodiments

The invention is not limited to the embodiments described above.

In particular, the segmentation implemented by the segmentation module and the calculations performed by the processor can be performed on the basis of a single image.

It has been seen above that the automatic score calculated depends on the mode of the histogram produced by the segmentation module, or also depends on the standard deviation of the histogram data.

Other parameters of the histogram may also be taken into account to calculate the score, including a skewness coefficient and kurtosis (histogram flattening coefficient).

The score may also depend on the coefficients associated with the segmentation program used. As it happens, the histograms produced by different segmentation programs are not perfectly identical; therefore, such coefficients further increase the correlation between the automatic score obtained and FEV1.

For example, the score can be calculated as follows:

$$\text{score} = a*(\text{standard deviation}) + b*(\text{mode}) + c*(\text{skewness coefficient}) + d*(\text{kurtosis coefficient}) + e*\left(\frac{\text{lung volume with a lung density above the calculated threshold}}{\text{total lung volume of the lung shown by the image}}\right)$$

where a, b, c, d and e are predetermined coefficients, at least one of the coefficients a, b, c, d and e depending on the image segmentation program used to implement the segmentation step.

For example, the score may be =1.7×Standard deviation+0.5×Mode+36×Skewness coefficient+0.1×Kurtosis coefficient−51×Score (Mode+3 SD).

The images may also be acquired by MRI. In this case, the histogram produced by segmentation of such images shows a distribution of lung signal intensities.

In other variants of the image processing method, the automatic score can be calculated not on the basis of a lung volume with a lung density above the calculated threshold, but on the basis of a lung volume with a lung density below the calculated threshold. In this case, the lower the score, the less dense the patient's lung.

The automatic score can advantageously be used to measure, in a patient, the extent of a pathology that induces diffuse lung bronchial disease, such as cystic fibrosis or primary ciliary dyskinesia or post-infectious or idiopathic diffuse bronchial dilatation.

The invention claimed is:
1. Method for automatically processing at least one image slice of a given part of at least one lung of a patient with a pathology that induces bronchial damage by diffuse dilatation of the bronchi of the lungs, the method comprising steps of:
   acquiring at least one image slice by CT scan,
   segmenting the image slice(s) of the given part of the lung, in order to produce a histogram characterizing the lung density of the given part of the lung, using the voxels of the image slice(s), each voxel being associated with a given lung density, calculating from the histogram a threshold corresponding to a threshold lung density, based on one or more characteristics of the histogram, a first characteristic being the mode of the histogram, the mode corresponding to the lung density most represented in the histogram of the image(s) of the given part of the lung, determining, from the image slice(s) of the given part of the lung, a lung volume having a lung density above or below the calculated threshold, corresponding to the sum of the voxels having a lung density above or below the calculated threshold, calculating, from the determined lung volume, an automatic score to monitor changes in the patient's bronchial involvement, wherein the threshold is based on at least two characteristics, and the second characteristic is a standard deviation of density values of the histogram.

2. Method according to claim 1, wherein the threshold is calculated using the following formula:

$$\text{threshold} = \text{mode} + N \cdot (\text{standard deviation})$$

where N is a predetermined value comprised in an interval ranging from 0 to 4.

3. Method according to claim 2, wherein N is a predetermined value comprised in an interval ranging from 1 to 2.

4. Method according to claim 1, in which the automatic score is a ratio between:

the lung volume having a lung density above or below the calculated threshold, and corresponding to the sum of the voxels having a lung density above or below the calculated threshold; on a total volume of the lung shown by the image(s), corresponding to the sum of all voxels in the image slice(s).

5. Method according to claim 1, wherein:

the lung volume with a lung density above the calculated threshold is determined (106) from the image(s) of the given part of the lung, the automatic score is the ratio between:

the lung volume having a lung density greater than the calculated threshold corresponding to the sum of the voxels having a lung density greater than the calculated threshold; on a total volume of the lung shown by the image(s), corresponding to the sum of all voxels in the image slice(s).

6. Method according to claim 1, wherein the images are taken over both lungs, or over one or more lobes of the lungs.

7. Method according to claim 1, wherein the images are acquired when the patient inspires.

8. Method according to claim 1, wherein the automatic score is also a function of a third characteristic, which is the skewness coefficient of the histogram, and a fourth characteristic, which is the kurtosis coefficient, and is calculated using the following formula $$\text{score} = a * (\text{standard deviation}) + b * (\text{mode}) +$$
$$c * (\text{skewness coefficient}) + d * (\text{kurtosis coefficient}) +$$
$$e * \left( \frac{\text{lung volume with a lung density above the calculated threshold}}{\text{total lung volume of the lung shown by the image}} \right)$$

where a, b, c, d and e are predetermined coefficients, at least one of the coefficients a, b, c, d and e depending on an image segmentation algorithm used to implement the segmentation step and where the skewness coefficient and the kurtosis coefficient refer to the histogram.

9. Method for measuring, in a patient, the extent of a pathology that induces bronchial damage by diffuse dilatation of the bronchi of the lungs, the measurement method comprising the processing method according to claim 1.

10. Device for automatically processing at least one image slice of a given part of at least one lung of a patient with a pathology that induces bronchial damage by diffuse dilatation of the bronchi of the lungs, the device comprising:

a module for acquisition of at least one CT image slice and for segmentation, configured to segment the image(s) of the given part of the lung, in order to produce a histogram characterizing the lung density of the given part of the lung, using the voxels of the image slice(s), each voxel being associated with a given lung density, at least one processor configured to:

calculate a threshold based on one or more characteristics of the histogram, a first characteristic being the mode of the histogram, the mode corresponding to the lung density most represented in the histogram of the image(s) of the given part of the lung, determine, from the image slice(s) of the given part of the lung, a lung volume with a lung density above or below the calculated threshold, corresponding to the sum of the voxels with a lung density above or below the calculated threshold, calculate, from the determined lung volume, an automatic score to monitor changes in the patient's bronchial involvement, the threshold being based on at least two characteristics, and the second characteristic is a standard deviation of density values of the histogram.

11. Method according to claim 9, wherein the pathology that induces bronchial damage by diffuse dilatation of the bronchi of the lungs is selected from the group consisting of cystic fibrosis, primary ciliary dyskinesia, post-infectious bronchial dilatation and idiopathic diffuse bronchial dilatation.

* * * * *